United States Patent [19]

Perkins et al.

[11] Patent Number: 5,718,238
[45] Date of Patent: Feb. 17, 1998

[54] FLUID COLLECTION CASSETTE IDENTIFICATION SCHEME

[75] Inventors: James Taylor Perkins, St. Charles; Peter Francis Appelbaum, Ballwin, both of Mo.

[73] Assignee: Storz Instrument Company, St. Louis, Mo.

[21] Appl. No.: 712,035

[22] Filed: Sep. 11, 1996

[51] Int. Cl.$^6$ .................................................. A61M 5/00
[52] U.S. Cl. ................. 128/760; 128/760; 128/771; 604/31
[58] Field of Search ................... 128/760, 771; 604/31, 50, 34; 435/291

[56] References Cited

U.S. PATENT DOCUMENTS

| | | | |
|---|---|---|---|
| 4,080,967 | 3/1978 | O'Leary | 128/214 |
| 4,214,237 | 7/1980 | Zissimopoulos | 340/686 |
| 4,349,814 | 9/1982 | Akehurst | 340/679 |
| 4,460,358 | 7/1984 | Somerville et al. | 604/250 |
| 4,515,535 | 5/1985 | D'Silva | 417/360 |
| 4,519,792 | 5/1985 | Dawe | 604/152 |
| 4,623,331 | 11/1986 | Cewers et al. | 604/65 |
| 4,689,304 | 8/1987 | Nelson et al. | 435/291 |
| 4,702,733 | 10/1987 | Wagner et al. | 604/34 |
| 4,798,580 | 1/1989 | DeMeo et al. | 604/30 |
| 5,653,243 | 8/1997 | Louke | 128/760 |

FOREIGN PATENT DOCUMENTS

| | | |
|---|---|---|
| 0 107 440 | 5/1984 | European Pat. Off. . |
| 2 069 063 | 8/1981 | United Kingdom . |

OTHER PUBLICATIONS

Kangaroo 330 Feeding Pump Operating Manual, Copyright 1983 Chesebrough–Pond's Inc.

*Primary Examiner*—Vincent Millin
*Assistant Examiner*—V. Srivastava
*Attorney, Agent, or Firm*—Montgomery W. Smith; Grant D. Kang

[57] ABSTRACT

The invention is a method of identifying whether a particular fluid collection cassette is designated to have a particular use, such as posterior surgery or anterior surgery. A reflux bulb attached to a fluid collection cassette has a material disposed on or in said reflux bulb in a predetermined location. When the reflux bulb is disposed on the fluid collection cassette, and the fluid collection cassette inserted into a housing, a sensor attached to the housing senses the existence, or non-existence of the material and sends a signal conveying the information to a main controller.

8 Claims, 3 Drawing Sheets

FLUID COLLECTION CASSETTE IDENTIFICATION SCHEME

BACKGROUND OF THE INVENTION

1. Field of the Invention

This invention relates to fluid collection cassettes used in surgical systems and, more particularly, to a scheme for identifying particular fluid collection cassettes.

2. Related Art

Ophthalmic microsurgical systems typically are classified in accordance with the surgical area of the eye to which the system is directed. Therefore, certain ophthalmic microsurgical systems are considered to be anterior systems, while others are considered to be posterior systems. Occasionally, these systems may be combined into one system which operates in both the anterior and posterior regions of the eye.

In all ophthalmic microsurgical systems, some type of fluid collection reservoir is utilized to collect fluid byproducts of the surgical operation. The fluid reservoir may take various forms. One form which is well known in the art is a fluid collection cassette which is a hard plastic cassette defining a fluid collection reservoir.

The prior art associated with such fluid collection cassettes utilize a reflux bulb member attached at one end to the inlet of the fluid collection cassette and at the other end to a tube which is itself connected to the hand piece.

Regardless of the type of operating procedure used, posterior or anterior, the size of the cassette remains constant. In fact, the only physical distinction that can be made between a cassette for posterior surgery and a cassette for anterior surgery is the size of the volume contained within the respective reflux bulbs. The volume contained within the posterior surgery reflux bulb is approximately 1/10 (one tenth) the volume of the anterior reflux bulb. This difference in volumes is made necessary from the very nature of the surgery itself.

During surgery, the fluid line between the handpiece and the fluid collection cassette may occasionally become clogged. When this occurs, a preferred way to unclog the line is to exert a back pressure pulse within the fluid line. This is accomplished by punching a first finger down onto a first portion of the reflux bulb, to pinch off and separate the fluid line into two parts. A second finger immediately adjacent the first finger, between the first finger and the handpiece, descends to also pinch a portion of the fluid line. When the second finger descends, back pressure is exerted along the length of the fluid line towards the handpiece and "blows out" or unblocks the fluid line.

The posterior reflux bulb volume is necessarily smaller than the anterior reflux bulb volume because posterior surgery occurs in the retinal portions of the eye. A large stream of fluid ejected from the handpiece into the retinal portions of the eye due to the manipulation of the reflux bulb could damage the eye. Accordingly, the cross-sectional area of the fluid line comprehended by the posterior reflux bulb is sized much smaller than the volume of the reflux bulb used with anterior surgery. In effect, the posterior reflux bulb will eject a much smaller stream of fluid in order to unclog the fluid line, which in posterior surgery may contain Balanced Salt Solution (BSS), vitreous, and blood, and in anterior surgery may comprise (BSS) and emulsified cataract.

Because the difference in volume of the posterior and anterior reflux bulbs are virtually impossible to distinguish externally with the naked eye, each type of reflux bulb is given a specific color. For posterior surgery, the color of the reflux bulb is yellow. For anterior surgery, the color of the reflux is blue.

Ophthalmic microsurgical systems are unable to distinguish automatically (mechanically or electrically) whether a posterior cassette or an anterior cassette was in use. In this situation, a dangerous volume of fluid may be expelled with each reflux, potentially damaging the eye. To avoid this situation from developing, the only safeguard to date is a reminder by the ophthalmic microsurgical system in an onscreen prompt to check the cassette, or written warnings associated with the packaging of the cassette. Accordingly, it still remains possible for human error to allow an anterior cassette to be used in a posterior surgery.

Accordingly, there is a need in the art to provide an automatic identification scheme which will permit a machine to identify whether a posterior or an anterior cassette is in the machine.

SUMMARY OF THE INVENTION

It is in the view of the above problems that the present invention was developed. The invention is a method of identifying the type or class of a particular fluid collection cassette, such as posterior or anterior cassettes. A reflux bulb attached to a fluid collection cassette has a material disposed on or in said reflux bulb in a predetermined location. When the reflux bulb is disposed on the fluid collection cassette, and the fluid collection cassette inserted into a housing, a sensor attached to the housing senses the existence, or non-existence of the material and sends a signal conveying the information to a main controller which can disable the surgical machine from operating until the proper cassette is inserted.

Two separate predetermined locations may be used, together with two sets of material and two sensors for a posterior reflux bulb, whereas a single predetermined location, material and sensor may be utilized to covey the existence of an anterior reflux bulb and to guarantee that the cassette originated from a source of guaranteed quality.

Further features and advantages of the present invention, as well as the structure and operation of various embodiments of the present invention, are described below in detail with reference to the accompanying drawings.

BRIEF DESCRIPTION OF THE DRAWINGS

The accompanying drawings, which are incorporated in and form a part of the specification, illustrate the embodiments of the present invention and together with the description, serve to explain the principles of the invention. In the drawings.

DETAILED DESCRIPTION OF THE PREFERRED EMBODIMENT

Figure 1:
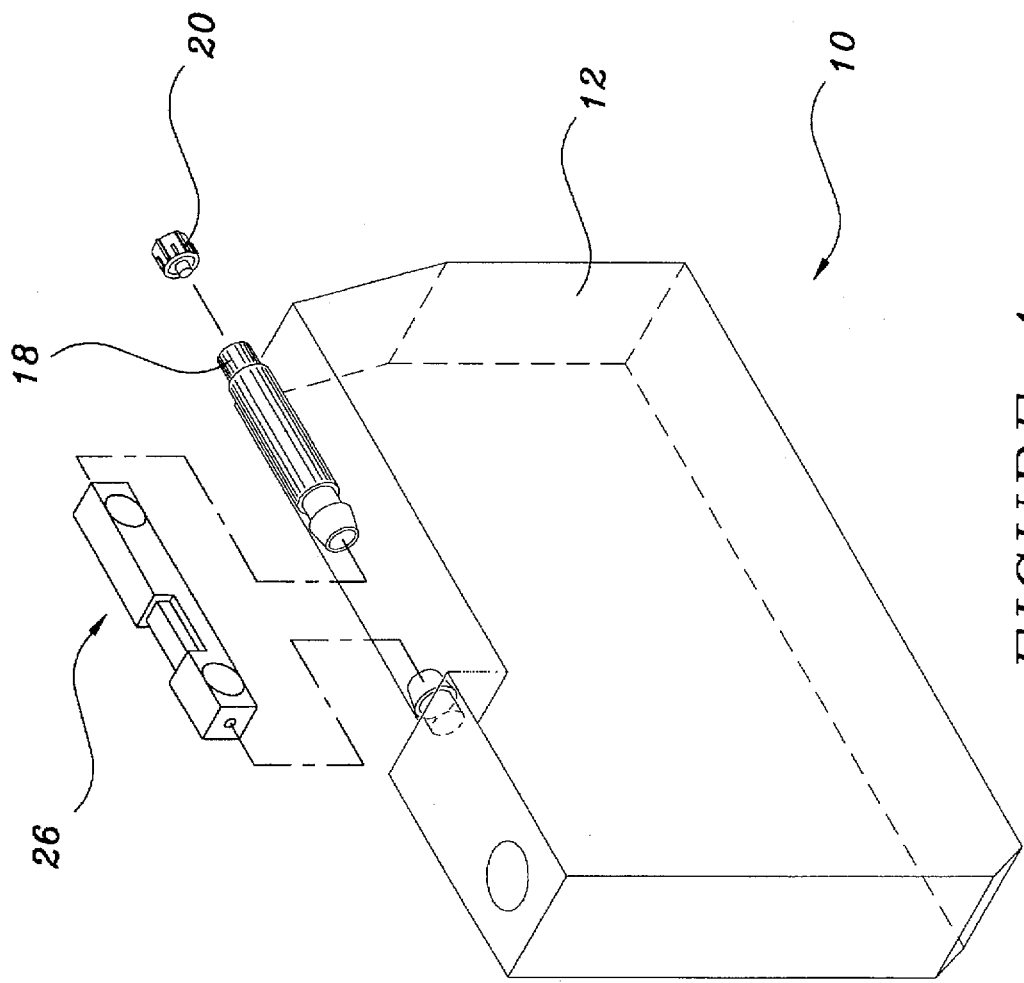
FIG. 1 illustrates an exploded view of a fluid collection cassette of the present invention.
Figure 1A:
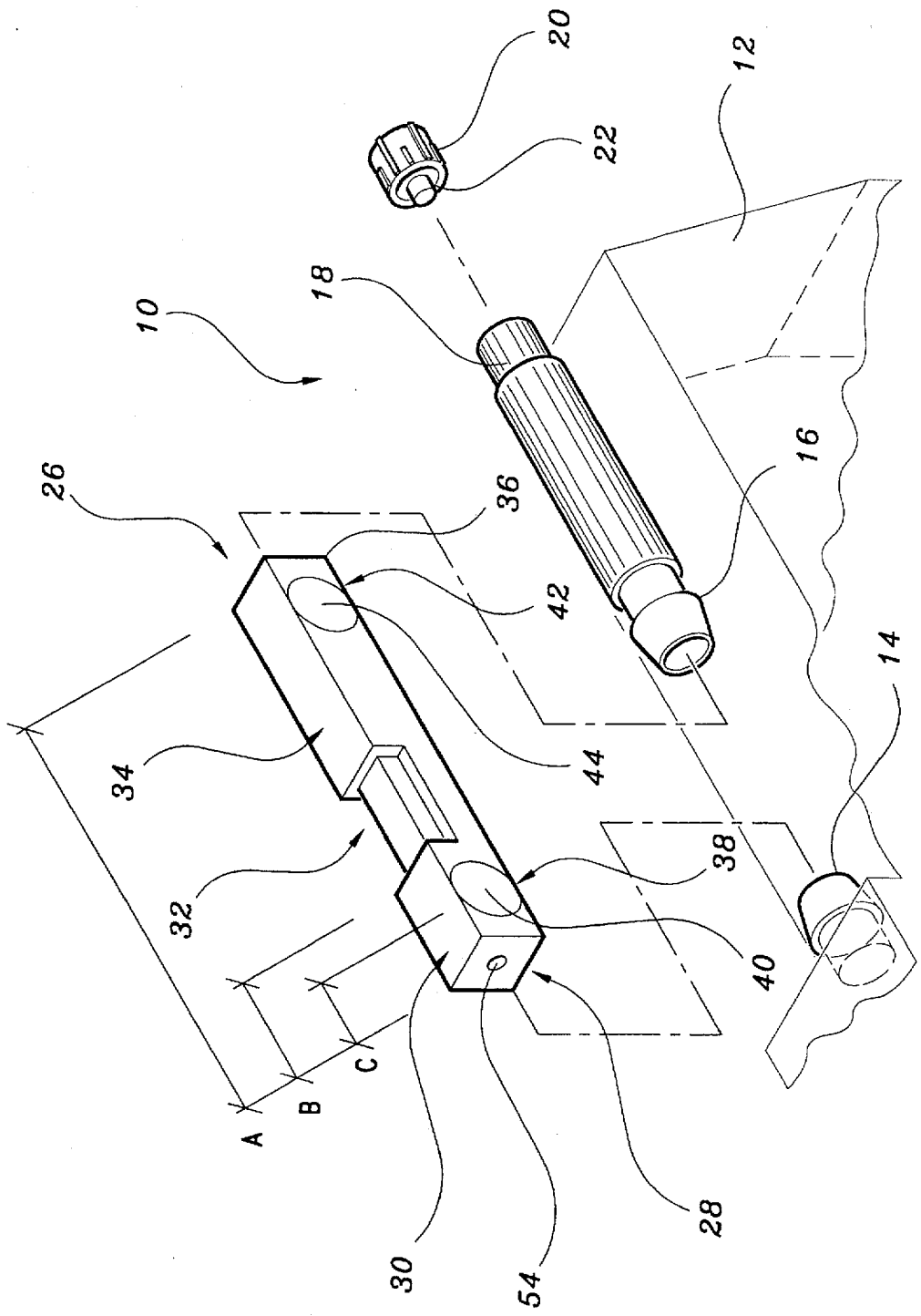
FIG. 1A illustrates an exploded detail view of the upper right portion of the fluid collection cassette illustrated in FIG. 1.

Referring to the accompanying drawings in which like reference numbers indicate like elements, FIG. 1 and FIG. 1A show an exploded view of a fluid collection cassette shown generally at 10 of the present invention. Fluid collection cassette 10 comprises a main body portion 12, an inlet tube barb 14, an outlet tube barb 16, outlet tube portion 18, and outlet tube adapter 20.

Preferably, main body portion 12, inlet tube barb 14, outlet tube barb 16 and outlet tube portion 18 are integrally molded. Outlet tube adapter 20 is provided with a stem 22 which is press fit into outlet tube portion 18. Alternatively, outlet tube adapter 20 may be provided with a stem 22 which is threaded (not shown) to mate with matching threaded portion (not shown) of outlet tube portion 18.

A reflux bulb 26 comprises first end 28 located in first body portion 30, second body portion 32, third body portion 34, and second end 36 located in third body portion 34. At a first predetermined location shown generally at 38 on reflux bulb 26, a first material 40 is disposed in or on reflux bulb 26. At a second predetermined location shown generally at 42, a second material is disposed in or on reflux bulb 26.

Preferably, first material 40 and second material 44 are both metal strips or metal circles to permit use as or in connection with a capacitive proximity switch. Alternatively, first and second materials, 40, 44, are of a material which would permit an alternate type of sensor to determine the existence or non-existence of first material 40 and second material 44 at first predetermined location 38 and second predetermined location 42, respectively.

First material 40 and second material 44 may be disposed in reflux bulb 26 which would raise the manufacturing cost, but would provide a greater guarantee of overall integrity. When first material 40 and second material 44 are both disposed on reflux bulb 26, preferably by adhesive, there is always some chance that one of the materials, 40, 44, could become disassociated with reflux bulb 26.

Overall, reflux bulb 26 has or may have an overall length of two inches. First body portion 30 may have a length of approximately ⅜ (three-eighths) of an inch. The distance from first end 28 to the center of first material 40 may be approximately 3/16 (three-sixteenths) inches. Similarly, the distance from second end 36 to the center of second material 44 may be approximately 3/16 (three-sixteenths) of an inch.

As FIG. 1 shows in exploded view, it is clear that the hole 54 defined by reflux bulb 26 extends through the length of reflux bulb 26. These holes are pushed onto and held by inlet tube barb 14 and outlet tube barb 16.

Reflux bulb 26 may assume a square cross-section measuring 5/16 (five-sixteenth) inch on each side.

Figure 2:
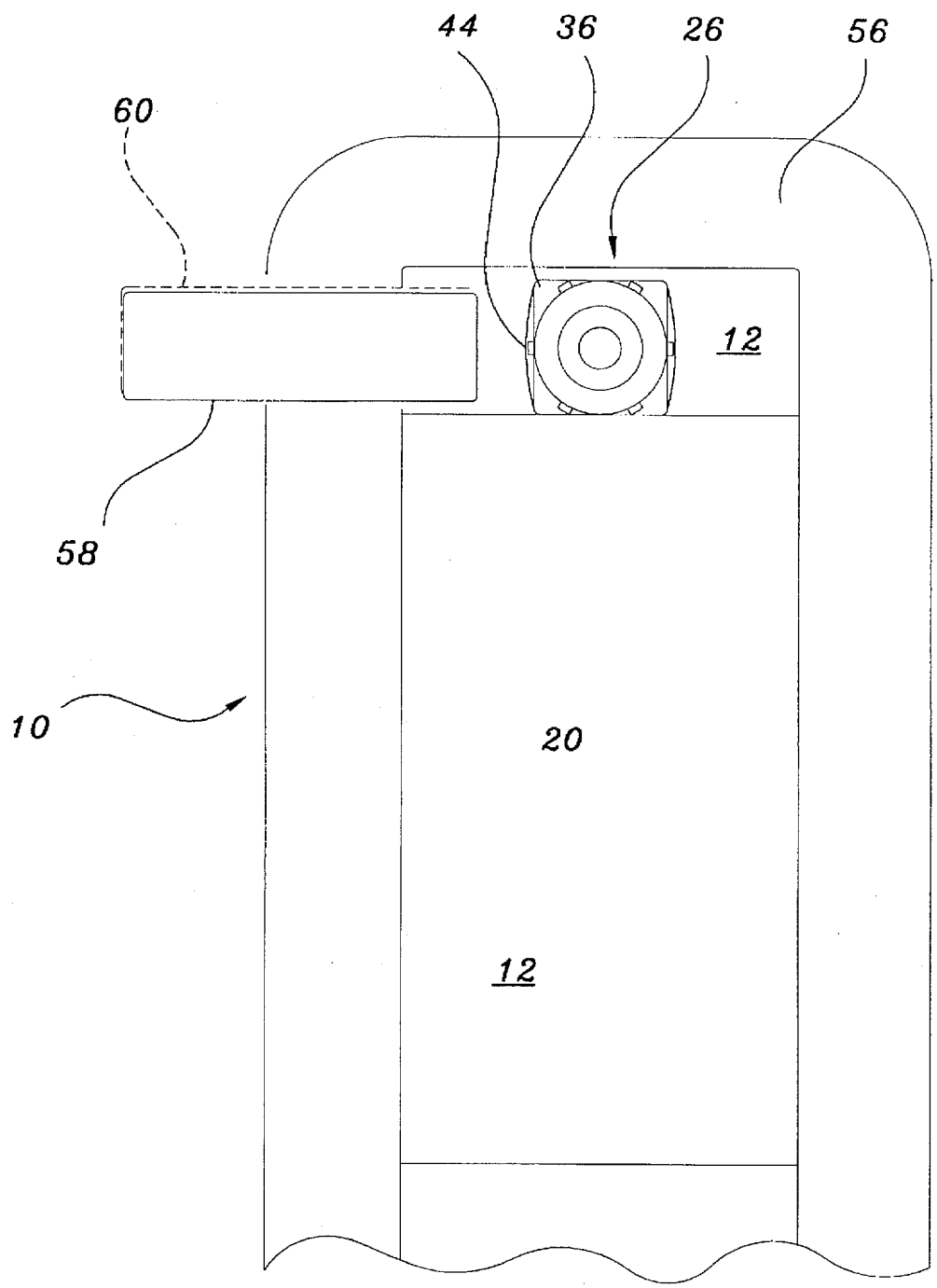
FIG. 2 illustrates the fluid collection cassette of the present invention disposed within a housing.

In operation, as shown in FIG. 2, fluid collection cassette 10 is disposed within housing 56. Housing 56 is located within an ophthalmic microsurgical system. Attached to housing 56 is a first sensor 58 and a second sensor 60. First and second sensors, 58–60, are preferably capacitive proximity switches and may be obtained readily from many electrical equipment manufacturers such as Balluff, Inc. of Florence, Ky. However, first and second sensors, 58–60, may also be of the sonic type (and the materials, 40, 44, respectively, suitable for reflecting sonic waves), or may be of the light (LED, laser, etc.) type (and the materials, 40, 44, respectively, suitable for reflecting light waves.

In operation, first and second sensors, 58–60, form one side of a capacitor, respectively, and first and second materials, 40, 44 form the other side of a capacitor, respectively. Accordingly, first and second sensors, 58–60, can sense the existence or non-existence of first material 40 and second material 44. The existence or nonexistence information is communicated from each sensor 58–60 to a controller which can act on this information and either enable or disable the operation of the ophthalmic microsurgical machine, using a logical well known in the art.

In view of the foregoing, it will be seen that the several objects of the invention are achieved and other advantages are attained. The embodiments were chosen and described in order to best explain the principles of the invention and its practical application to thereby enable others skilled in the art to best utilize the invention in various embodiments and with various modifications as are suited to the particular use contemplated. As various modifications could be made in the constructions and methods herein described and illustrated without departing from the scope of the invention, it is intended that all matter contained in the foregoing description or shown in the accompanying drawings shall be interpreted as illustrative rather than limiting. For example, the predetermined locations, 38 and 42, are not required to be on the same side of reflux bulb 26. Another modification falling within the scope of the present invention involves using three or more predetermined locations in conjunction with the application of sensing material at each location to assist in identifying a function other than anterior or posterior. Thus, the breadth and scope of the present invention should not be limited by any of the above-described exemplary embodiments, but should be defined only in accordance with the following claims appended hereto and their equivalents.

What is claimed is:

1. A method of identifying a fluid collection cassette comprising the steps of:
   (a) disposing a material to be sensed in a first predetermined location on a reflux bulb; and
   (b) disposing said reflux bulb on said fluid collection cassette such that a sensor for sensing said material may sense the existence of said material.

2. A method of identifying a fluid collection cassette according to claim 1, wherein the step of disposing a material to be sensed in a first predetermined location on a reflux bulb is accomplished by attaching said material to a surface of said reflux bulb.

3. A method of identifying a fluid collection cassette according to claim 1, further comprising the steps of:
   (c) adapting a housing to receive said fluid collection cassette; and
   (d) attaching a first sensor to said housing at a location which will permit said first sensor to sense the existence of said material when said fluid collection cassette is disposed in said housing.

4. A method of identifying a fluid collection cassette according to claim 1, further comprising the following step between steps (a) and (b):
   (aa) disposing a material to be sensed in a second predetermined location on a reflux bulb;
   (c) adapting a housing to receive said fluid collection cassette; and
   (d) attaching a first sensor to said housing at a location which will permit said first sensor to sense the existence of said material at said first predetermined location when said fluid collection cassette is disposed in said housing; and
   (e) attaching a second sensor to said housing at a location which will permit said second sensor to sense the existence of said material at said second predetermined location when said fluid collection cassette is disposed in said housing.

5. A method of identifying a fluid collection cassette comprising the steps of:
   (a) disposing a material to be sensed in a first predetermined location in a reflux bulb; and (b) disposing said reflux bulb on said fluid collection cassette such that a sensor for sensing said material may sense the existence of said material.

6. A method of identifying a fluid collection cassette according to claim 5, wherein the step of disposing a material to be sensed in a first predetermined location in a reflux bulb is accomplished by attaching said material under the outer surface of said reflux bulb.

7. A method of identifying a fluid collection cassette according to claim 5, further comprising the steps of:

(c) adapting a housing to receive said fluid collection cassette; and (d) attaching a first sensor to said housing at a location which will permit said first sensor to sense the existence of said material when said fluid collection cassette is disposed in said housing.

8. A method of identifying a fluid collection cassette according to claim 5, further comprising the following step between steps (a) and (b):

(aa) disposing a material to be sensed in a second predetermined location in a reflux bulb;

(c) adapting a housing to receive said fluid collection cassette; and (d) attaching a first sensor to said housing at a location which will permit said first sensor to sense the existence of said material at said first predetermined location when said fluid collection cassette is disposed in said housing; and (e) attaching a second sensor to said housing at a location which will permit said second sensor to sense the existence of said material at said second predetermined location when said fluid collection cassette is disposed in said housing.

\* \* \* \* \*